United States Patent [19]
Gillard et al.

[11] 4,036,222
[45] July 19, 1977

[54] AUTOMATIC ELECTRONIC APPARATUS FOR MEASURING THE BRONCHIAL RESISTANCE AND THE ELASTANCE OF THE PULMONARY TISSUE

[75] Inventors: Claude Gillard, Brussels; Marcel Mauroy, Nouvelles, both of Belgium

[73] Assignee: Soram S.A., Geneva, Switzerland

[21] Appl. No.: 568,330

[22] Filed: Apr. 15, 1975

[30] Foreign Application Priority Data

May 8, 1974  Belgium ................................. 144095

[51] Int. Cl.² .............................................. A61B 5/08
[52] U.S. Cl. .................................................. 128/2.08
[58] Field of Search .............. 128/2.08, 2.07, DIG. 29

[56] References Cited

U.S. PATENT DOCUMENTS

| 3,598,111 | 8/1971 | Kahn | 128/2.08 |
| 3,621,833 | 11/1971 | Crane | 128/2.08 |
| 3,797,479 | 3/1974 | Graham | 128/2.08 |
| 3,902,481 | 9/1975 | Bargeton et al. | 128/2.08 |
| 3,903,875 | 9/1975 | Hughes | 128/2.08 |
| 3,924,612 | 12/1975 | Dempster et al. | 128/2.08 |

FOREIGN PATENT DOCUMENTS

| 1,563,125 | 2/1968 | France | 128/2.08 |
| 474,996 | 8/1969 | Switzerland | 128/2.08 |

OTHER PUBLICATIONS

Gulesian, "An Instrument . . . MEFV Parameters", IEEE Trans. on Bio-Med. Eng. Sept. 1971, pp. 378-379.
Murphy et al., "A Dynamic Complance Computer: Comparison . . . Man", J. of App. Phys., vol. 36, No. 5, May 1974, pp. 629-633.
Hilberman et al., "On-line Assessment . . . acutely ill", JAAMI, vol. 6, No. 1, Jan.-Feb. 1972, pp. 65-69.
Comroe et al., "Design of a Body Plethys . . . Physiology.", J. Applied Physiology, vol. 14, 1959, May, pp. 439-444.

*Primary Examiner*—Robert W. Michell
*Assistant Examiner*—Lee S. Cohen
*Attorney, Agent, or Firm*—Stevens, Davis, Miller & Mosher

[57] ABSTRACT

The invention relates to medical science.

According to the invention, the resistance to air flow through the bronchial tracts and the elastance of the pulmonary tissue are measured and displayed, starting from signals which represent the respiratory air flow and the variation in endothoracic pressure, by means of an apparatus which comprises a flow signal preamplifier, a pressure signal preamplifier, two automatic calculating devices and an electronic control combination.

The apparatus makes it possible to use endothoracic pressures measured via the central venous system and can possess an alarm signal which is triggered automatically if the values displayed are memorized values.

9 Claims, 7 Drawing Figures

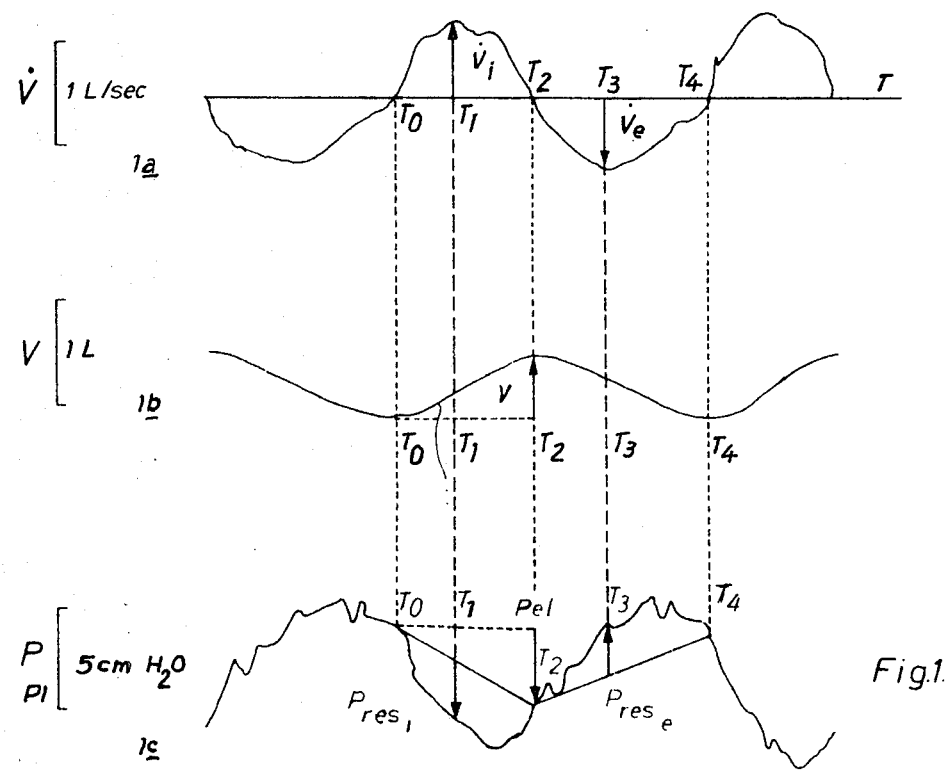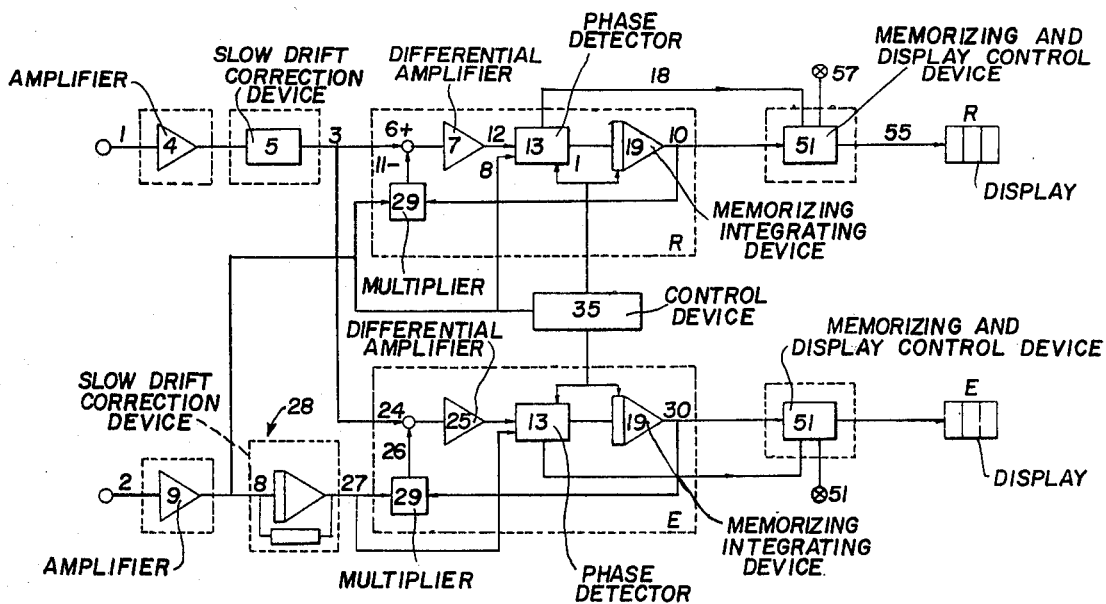

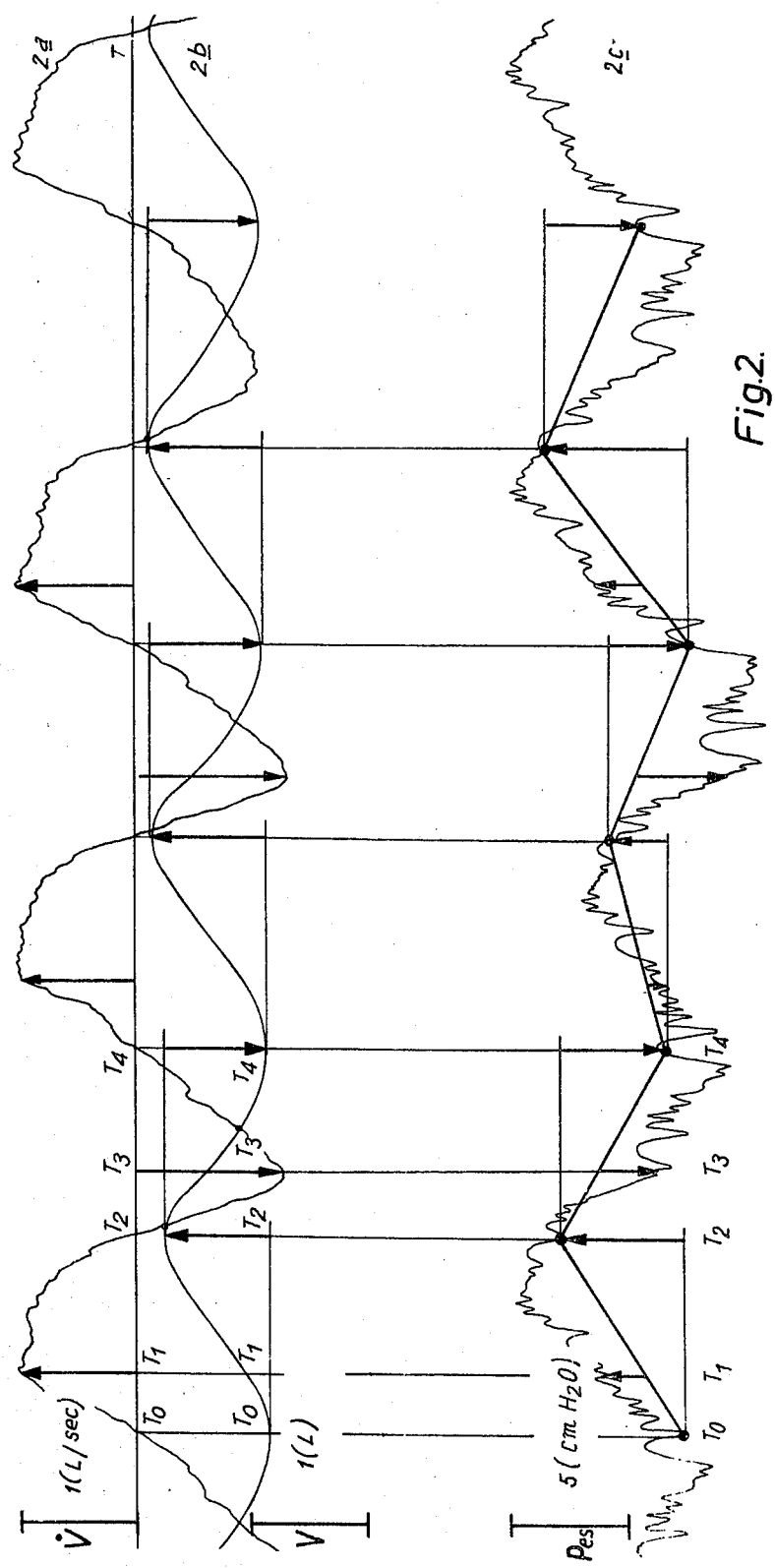

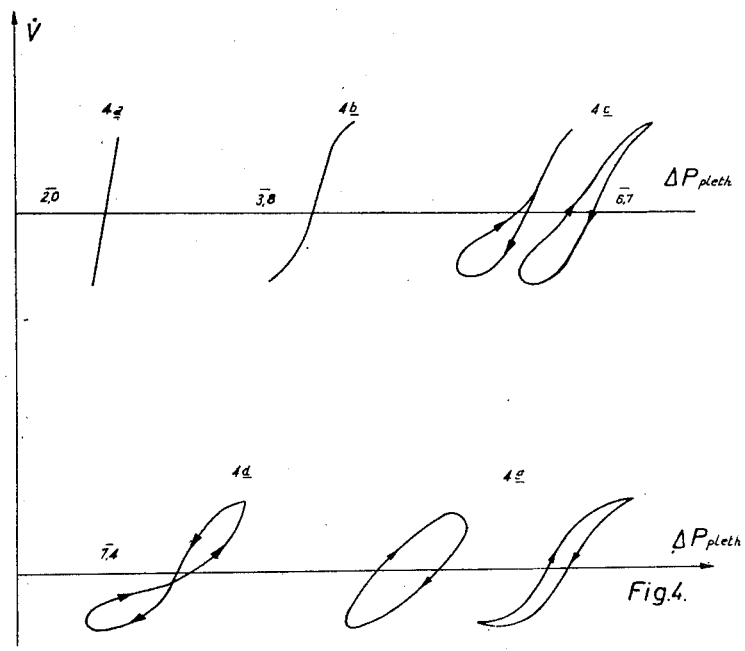
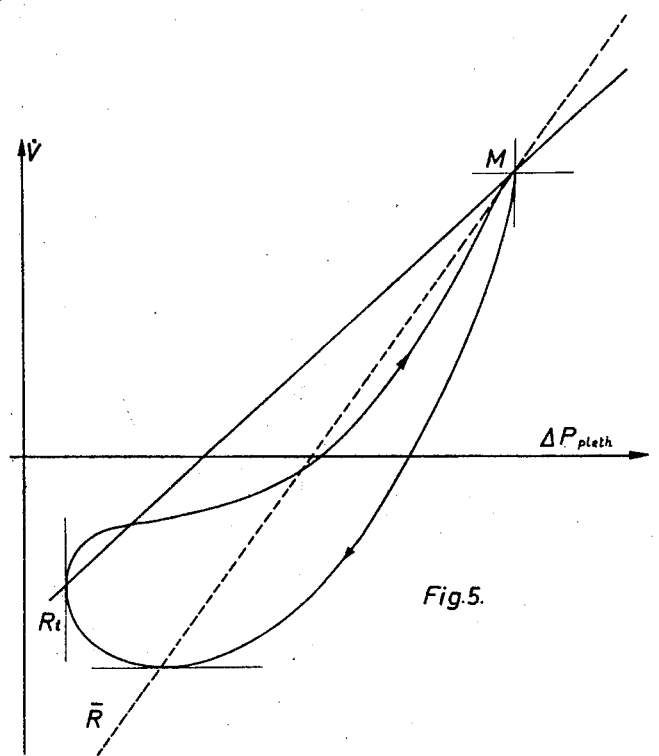

AUTOMATIC ELECTRONIC APPARATUS FOR MEASURING THE BRONCHIAL RESISTANCE AND THE ELASTANCE OF THE PULMONARY TISSUE

The subject of the invention is an automatic electronic apparatus for measuring and displaying, continuously and simultaneously, the resistance to air flow through the bronchial tracts and the elastance of the pulmonary tissue, these parameters being denoted respectively by the symbols R and E, starting from signals which represent the respiratory air flow and the variation in endothoracic pressure.

It is known that the determination of these parameters by medical practitioners is of very great importance for detecting either pathological conditions of the respiratory tracts, or deteriorations in these tracts due, for example, to accidents. For this purpose, medical science uses various methods which have, in common, the fact that the variation in endothoracic pressure is obtained by esophageal catheterization. It is convenient to differentiate between them depending on whether they make it possible to determine both parameters together or separately.

According to the method for determining R and E simultaneously, the variation in endothoracic pressure, the respiratory air flow through the mouth, and the variation in pulmonary volume (determined by continuous integration of the flow) are recorded at the same instant, as a function of time, and this makes it possible to determine, by graphical analysis, a value for the bronchial resistance (R) and for the elastance (E) of the pulmonary tissue, for half a respiratory cycle, the inspiration and expiration phases being analyzed separately.

Its main disadvantage is the fact that esophageal catheterization is necessary in order to obtain the endothoracic pressure; now, this operation is frequently poorly tolerated by the patient and it cannot be repeated easily. Moreover, the artefacts introduced into the esophageal barogram by heart beats are often large and interfere with the exact determination of the pressure values contemporaneous with flow reversals or with moments of maximum flow. And finally, the graphical analysis and the calculations which result therefrom are long, especially if it is desired to investigate a sufficient number of respiratory half-cycles.

According to the so-called interruption method for determining R, the respiratory air flow through the mouth and the pressure in the mouth are recorded simultaneously with time.

When the flow is briefly interrupted, there is, in principle, instantaneous equalization of the pressure in the mouth and of the pressure in the alveoli. The difference between the pressure in the mouth and the pressure in the alveoli evaluated in this way is related to the corresponding air flow and makes it possible to estimate the parameter R.

In practice, however, as soon as a certain degree of ventilation asynchronism exists, and this occurs very frequently in pathology, the time necessary to equalize the pressures in the alveoli and the mouth is longer and frequently exceeds the duration of the interruption. Consequently, interruption is ceased before complete equalization of the pressures, the pressure in the alveoli is thus underestimated and the determination of the parameter R is very erroneous.

According to the so-called plethysmographic method for determining R, the respiratory air flow through the mouth and the intraplethysmographic pressure, which is representative of the intra-alveolar pressure taking into account a correction introduced by the ratio, established beforehand, of the volume of the plethysmographic chamber to the pulmonary volume at rest, are recorded simultaneously using rectangular co-ordinates.

The method gives correct and very reproducible results for bronchial resistances R which are normal or which deviate from the norm to only a relatively small extent.

However, if the inherent elasticity of the bronchial walls intervenes to an appreciable extent, this results in a phase displacement which is sometimes large and can frequently even vary during one and the same respiratory cycle between the signal corresponding to the air flow through the mouth and the signal corresponding to the "alveolar" pressure.

The drawing of the tangents at the points of inflexion of the pressure/flow diagrams, which is easy for some cases, becomes difficult for others.

Moreover, although the linear approximation is justified for curves of a simple type, it is certainly no longer justified for curves which include phase displacement and considerable distortion. The linear approximation thus completely ignores the change in the phenomenon between two so-called characteristic points which are themselves determined in a frequently arbitrary manner. The disagreements to be found in the literature provide adequate proof of these inaccuracies: the resistances are sometimes determined at maximum flow, and sometimes at maximum pressure, the so-called total resistances of the German authors, and are sometimes determined only at the end of expiration, and the like.

According to a method for determining E, the endothoracic (esophageal) pressure and the variation in the pulmonary volume (measured by spirography or integration of the pneumotachygraphic flow) are recorded simultaneously using rectangular co-ordinates.

The parameter E is determined by the slope of the straight line joining the points corresponding to the maximum pulmonary volume and to the minimum pulmonary volume (reversal of the flow).

As in the first method mentioned, esophageal catheterization is necessary in order to obtain the endothoracic pressure: the methodological requirements are very strict as to the diameter and the length of the catheter, the quality of the esophageal bulb, and the characteristics and performances of the probes; these requirements ae such that the slightest departure can lead to errors which are sometimes considerable.

In addition to the disadvantages characteristic of each of them, these methods provide E and R values which are impossible to define rigorously.

This is due essentially to the fact that the measured values of these parameters depend, on the one hand, on the amplitudes of the signals observed because the system investigated is non-linear, and on the other hand, on the spectral content of the signals observed, which is highly subject to perturbations such as the artefacts introduced into the esophageal pressure signal by heart beats or by esophageal contractions.

Some authors have used a measuring technique familiar to engineers, namely the method of the first harmonic which appreciably reduces the effect of sudden perturbations. The method which they propose requires the use of band-pass filters tuned to the respiration frequency and proceeds thereafter by graphical analysis as is conventionally carried out. This method possesses a serious disadvantage: in fact, in order to be effective, these filters must be very selective. They thus require that the respiration frequency be very stable and, in practice, this can be achieved only in the case of trained individuals.

The apparatus according to the invention makes it possible to eliminate all these disadvantages. It considerably reduces the effects of the perturbations mentioned above, calculates continuously and displays numerically the values of the two parameters, namely resistance and elastance. It calculates automatically the resistance of the bronchial tracts and the elastance of the pulmonary tissue, starting from two electric signals, one proportional to the flow through the mouth and the other proportional to the endothoracic pressure. Its measuring device is also almost completely insensitive both to slow drifts of these signals and to their harmonic components, to cardiac components or to adventitious noise.

The present methods mentioned above have, moreover, the common disadvantage of being able to be applied only for greatly restricted periods of time. The dwell time in the plethysmographic chamber and the application of oral interruption are materially possible only for a few minutes. Toleration of the esophageal probe is also restricted to a few tens of minutes at the most.

Due to its high degree of rejection of variations in systolic/diastolic pressure, the apparatus according to the invention makes it possible to use the central venous pressure for measuring the respiratory component of the variation in endothoracic pressure. Now, endovenous catheters can remain in position for several consecutive days and even for several weeks. Very frequently, in the case of patients who have undergone operations or who are under intensive care, the endovenous catheters are placed in position as a matter of routine, via the sub-clavian tract, and consequently the determination of the endothoracic pressure requires no further medical intervention. Moreover, the esophageal tract remains free for the requirements relating to intensive care, namely feeding of the patients, aspiration in cases of surgical digestive pathology, and the like.

Under these conditions, all that then remains to be obtained, for example by pneumotachygraphy, is the air flow through the mouth of a patient, whether he is conscious or unconscious, and breathing freely or under assisted respiration, in order to be able to determine continuously the values of the parameters R and E.

Furthermore, the overall size of the present apparatuses, and mainly of the plethysmograph, makes it practically impossible for them to be used in operating theatres and in intensive care units, and more especially as almost insurmountable sterilization problems would result therefrom. In contrast, the apparatus according to the invention, which is of very small overall size, can be in general use for intensive care purposes or during surveillance after operations and even during operations, sterilization problems being practically non-existent and the very small overall size enabling it to be introduced into the operating theatre without hindering the medical staff.

The automatic electronic apparatus according to the invention for measuring and displaying, continuously and simultaneously, the resistance to air flow through the bronchial tracts and the elastance of the pulmonary tissue, these parameters being denoted respectively by the symbols R and E, starting from signals which represent the respiratory air flow and the variation in endothoracic pressure, comprises a flow signal preamplifier, a pressure signal preamplifier and a flow signal integrator equipped with a mean value correcting device, an electronic control unit, and, for each of the parameters R and E, an automatic system which possesses a differential amplifier, a phase detector which operates by multiplication, a device for calculating the mean value over each respiratory cycle, an integrator and a multiplier, wherein the differential amplifier gives the difference between the pressure signal and, for measuring the parameter R, a signal which is proportional, by a factor of approximately alpha, to the flow. This difference is compared, in phase, with the flow signal at each respiratory cycle and at a moment defined by the electronic control unit, and the result of this comparison is integrated to give the said proportionality factor alpha, the combination being produced so as to achieve, after a few respiratory cycles, a stable equilibrium for which the phase difference between the flow signal and the signal equal to the difference between the pressure signal and the signal proportional to the flow is equal to 90°, which corresponds to a practically zero output signal from the phase detector and to a constant proportionality factor alpha which, under these equilibrium conditions, is equal to the bronchial resistance R. The parameter E is measured in a similar manner by calculating the difference between the pressure signal and a signal which is proportional, by a factor of approximately beta, to the volume, this factor beta being, under the equilibrium conditions of this second automatic measuring system, equal to the value of the elastance E of the pulmonary tissue.

The pressure preamplifier and the flow integrator which feed the two automatic measuring combinations described, are individually equipped with a control loop intended to nullify the mean value of the pressure variation or of the volume variation over each respiratory cycle, so that any slow drift of these signals has no appreciable effect on the accuracy of the measurement of the parameters R and E.

The two automatic systems for measuring the parameters R and E provide signals which are able to measure the state of equilibrium imbalance of each of them and to feed a decision-making and memory-storing electronic unit suitable for authorizing numerical display of the parameters when an equilibrium position is achieved, but which triggers an alarm and retains the last correct result in its memory as soon as different experimental conditions arise, the electronic unit making it possible, moreover, for the two automatic systems to be reset to zero when the user intervenes.

According to the invention, the apparatus makes it possible to use a volume signal measured by variation in deep thoracic impedance and a flow signal constructed from a volume signal shunting device.

Moreover, it makes it possible to use endothoracic pressures measured via the central venous system.

The constituent parts of the apparatus according to the invention can be located in the same casing with or without the flow integrator, with one or the other automatic combination for measuring R or E, and with or without the decision-making and memory-storing electronic unit.

The attached drawings comprise five figures intended to illustrate the conventional methods for determining the parameters R and E and two figures which represent, by way of example, one embodiment of the invention.

Because the technology of electronic circuits is undergoing rapid development, it is obvious that the circuits represented are given solely to explain the way in which the device operates, and that they could easily be replaced by equivalent circuits of comparable performance, which may or may not be miniaturized, without having a detrimental effect on the scope of the invention. In particular, it is possible to replace the integrator which provides the alpha signal by an amplification or integration device, the gain of which would be adjusted in accordance with the flow signal and/or the respiration frequency. It is also possible to carry out, by a numerical method, all or part of the operations which, in this embodiment, are carried out by an analogical method.

It is also to be understood that all the symbols represented but not described in this text possess their normal meaning in electronics and thus fulfil their customary functions.

FIGS. 1 and 2 represent graphs obtained according to the conventional method for determining the parameters R and E simultaneously;

FIGS. 4 and 5 represent flow/pressure diagrams obtained using the plethysmographic method;

FIG. 6 represents the block diagram of the apparatus according to the invention.

The conventional curves 1a, 1b and 1c (FIG. 1) represent respectively, as a function of time T, the air flow through the mouth $\overset{\circ}{V}$ (liters/second), the variation in pulmonary volume V (liters) and the variation in pleural pressure $P_{pl}$ (cm of water), the scale of these sizes being indicated on the left of the figure. The part of each of the curves lying within the time intervals $T_0$–$T_2$ and $T_2$–$T_4$ corresponds respectively to the inspiration and expiration processes of a respiratory cycle. The ordinates $\overset{\circ}{V}_i$ and $\overset{\circ}{V}_e$, at times $T_1$ and $T_3$, represent respectively the maximum inspiration and expiration flows to which the drops in inspiration resistive pressure $Pres_i$ and expiration resistive pressure $Pres_e$ correspond. The ordinate $P_{el}$ represents the variation in elastic pressure.

The pulmonary compliance $Cl$, which is the inverse of the elastance $E$ of the pulmonary tissue, is obtained graphically from the relationship $$Cl = V/P_{el} = 1/E$$

and the inspiration resistance $R_i$ and the expiration resistance $R_e$ are obtained from the relationships $$R_i = Pres_i/\overset{\circ}{V}_i$$

and $$R_e = Pres_e/\overset{\circ}{V}_e$$

The conventional curves 2a, 2b and 2c (FIG. 2) are similar to those of FIG. 1, except that the variation in esophageal pressure $P_{es}$ has been used as the signal representative of the variation in endothoracic pressure.

The drift of the curves from cycle to cycle and the complexity of the curve 2c will be noted.

Figure 3:
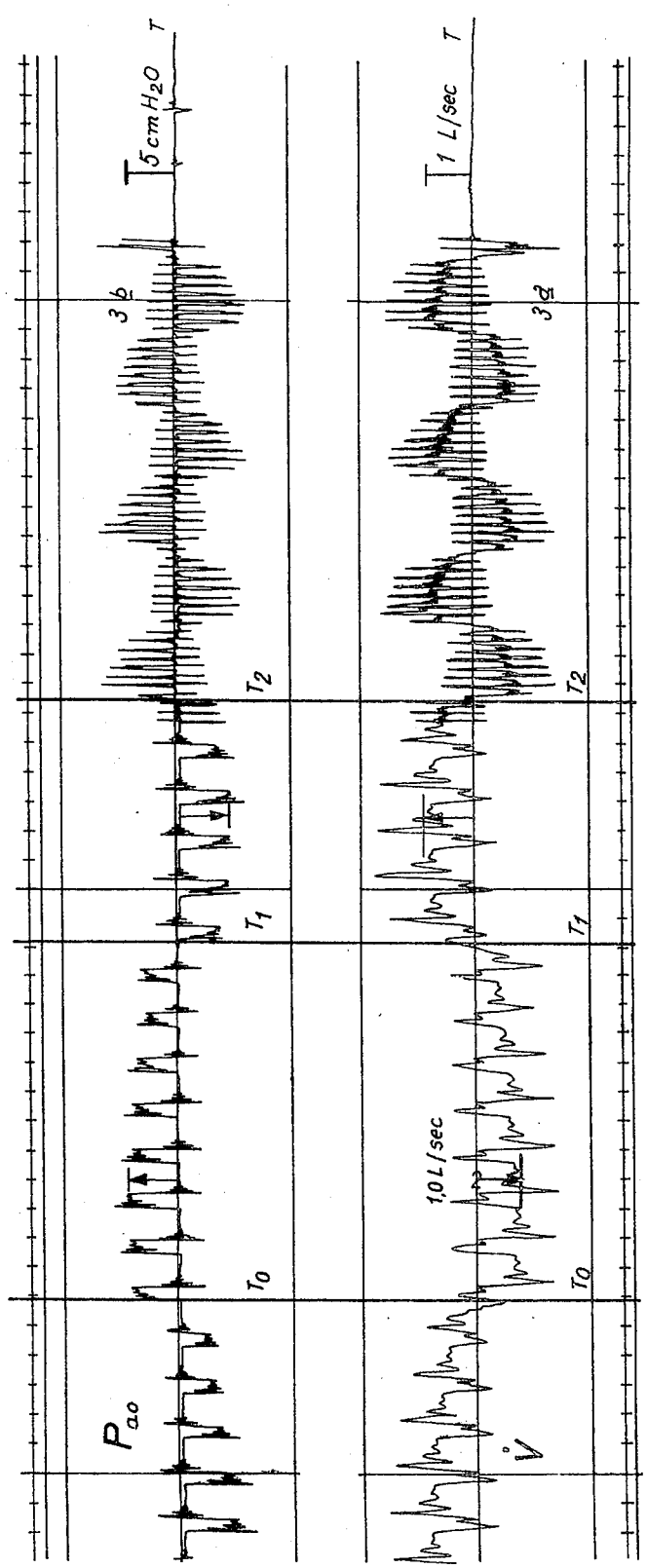
FIG. 3 represents graphs illustrating the conventional so-called interruption method for determining the parameter R.

The conventional curves 3a and 3b (FIG. 3) represent respectively the relationship of interrupted flow $\overset{\circ}{V}$ in liters/second and the variation in pressure in the mouth $P_{ao}$ in cm of water as a function of the time T, the corresponding scales being indicated on the right of the figure. The part of each of the curves lying within the time intervals $T_0$–$T_1$ and $T_1$–$T_2$ correspond respectively to the expiration and inspiration processes of a respiratory cycle. The resistances measured are $$R_e = P_{ao}/\overset{\circ}{V}_e = 5.5/1.0 = 5.5 \text{ cm H}_2\text{O/liters/second.}$$

and $$R_i = P_{ao}/\overset{\circ}{V}_i = 5.5/1.1 = 5.0 \text{ cm H}_2\text{O/liters/second.}$$

In the conventional diagrams 4a to 4e (FIG. 4), the abscissa measures the variation in intra-plethysmographic pressure, in cm of water, and the ordinate measures the respiratory air flow through the mouth in liters/second. The slope of the curves is considered to give the mean value of the parameter R.

It is seen that the slope is obvious for a curve of the type 4a. For a diagram of the type 4b, the line of the tangent at the point of inflection (the slope) is still easy to obtain, and the linear approximation may be justified, but this line becomes difficult for curves of the types 4c to 4e, and the approximation is no longer justified.

In the conventional curve of FIG. 5, the part above the abscissa corresponds to inspiration, and the negative part corresponds to expiration. The slopes drawn from the point M, flow and pressure maximum, represent either the "total" resistances $R_t$ measured at maximum pressure, or the "mean" resistances R measured at maximum flow.

As has been shown, the method breaks down as soon as the bronchial resistances depart from the normal.

Figure 7:
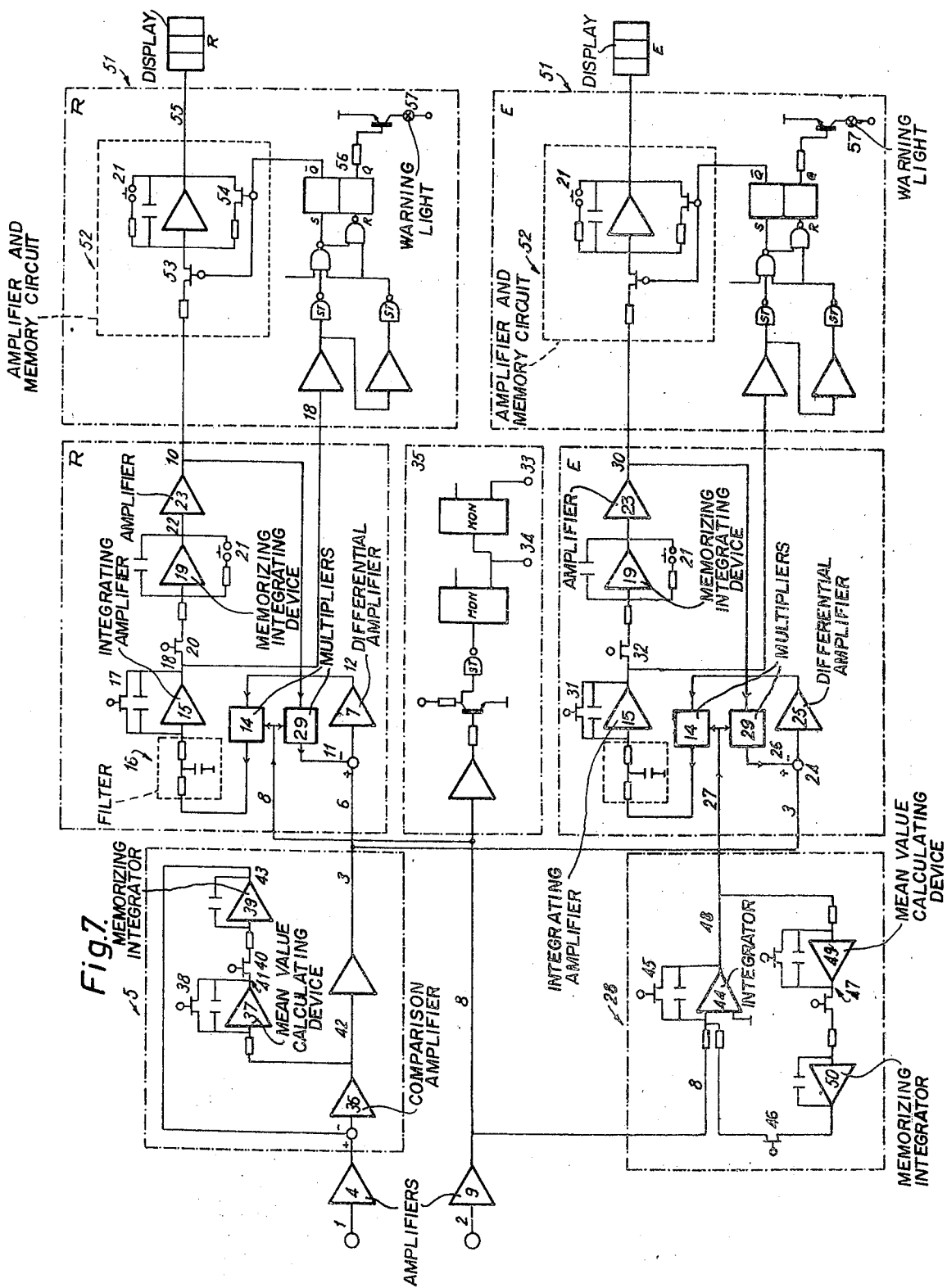
FIG. 7 represents the basic circuit of the electronic unit of the apparatus according to FIG. 6.

When a variation in endothoracic pressure 1 (FIGS. 6 and 7) and an air flow 2 through the mouth are measured on a patient, in accordance with the invention, the pressure signal 3, amplified beforehand by an amplifier 4 and corrected for its slow drift by a device 5, is applied to the input 6 of a differential amplifier 7 while the flow signal 8 amplified beforehand by an amplifier 9 and multiplied in multiplier 29R by a voltage alpha appearing at 10 is applied to the second input 11 of the differential amplifier 7. The difference 12 between these two signals is compared in phase with the flow signal 8, employing a phase detector 13. The latter consists of a multiplier 14 and a device for calculating the mean value over one respiratory cycle, realized by means of an integrating amplifier 15 combined with a filter 16 and an electronic switch 17. The latter normally remains open; it closes for a very short moment during each respiratory cycle in order to reset the integrating device 15 to zero.

The signal 18 which appears at the output of this integrator, before closing the switch 17, represents the mean value desired and the latter is almost proportional to the difference relative to 90° of the phase displacement of the difference signal 12 relative to the flow signal 8. The phase differences 18, measured at each respiratory cycle, are stored by a memorizing integrating device 19 consisting of an integrating amplifier combined with an electronic switch 20 and a zero-resetting manual switch 21 which is normally open. Prior to closing the switch 17, the switch 20 is closed for a very short moment, so as to transfer the signal 18 to the memorizing integrator 19. The output voltage 22 from the latter thus increases at each respiratory cycle until its value alpha 10, amplified beforehand by a device 23, is equal to R and this leads to a phase difference 18 equal to zero and thus to an equilibrium voltage alpha 10 which is constant.

The automatic combination for measuring the parameter E of the apparatus operates in an identical manner except that the amplified and corrected pressure signal 3 is applied to the input 24 of a differential amplifier 25, the second input 26 of the latter receiving the volume signal 27, an integral of the amplified flow signal 8, which has been corrected for its slow drift by a device 28 and multiplied, by means of a device 29, by a voltage beta appearing at 30.

The electronic switches 17, 31 and 20, and 32 are controlled respectively by pulses 33 and 34 created by a control device 35 from the flow signal 8. The two successive pulses 33 and 34 are constructed by means of conventional logical circuits passing to zero flow at the end of inspiration.

The device 5 for correcting for slow drift of the pressure signal comprises a comparison amplifier 36, a device 37 for calculating the mean value over one respiratory cycle equipped with an electronic switch 38 controlled by the pulse 33 and a memorizing integrator 39 equipped with the electronic switch 40 controlled by the pulse 34.

The switch 38, which is normally open, closes in each respiratory cycle for a very short moment in order to enable the device 37 to be reset to zero. The signal 41 which appears at the output of the device 37 before closing 38 represents the mean value of the pressure signal 42. These mean values measured at each respiratory cycle are stored by the memorizing integrator 39.

The output voltage 43 thus increases from one respiratory cycle to the following respiratory cycle until its value, subtracted from the amplified pressure signal 1, leads to a signal 42, the mean value of which is zero. This state of equilibrium can be achieved after a few respiratory cycles and even in a single cycle if the gain of the devices 37 or 39 varies suitably in accordance with the respiratory cycle.

The device 28 for correcting for the slow drift of a flow integrator 44 operates on a principle similar to that of the device 5; it comprises, in addition to the latter, an electronic switch 45 controlled by the pulse 34 and an electronic switch 46 controlled by the pulse 33. The switch 45 provided for resetting the integrator to zero at each respiratory cycle and the switch 46 applies, to the input of this integrator, a pulse of short duration and of height such that the mean value 47 of the volume signal 48 calculated by the device 49 is zero.

Once again, this state of equilibrium is achieved after a few respiratory cycles and even in a single cycle, if the gain of the integrator 50 varies suitably in accordance with the respiratory cycle.

The memorizing and display-control device 51 of the apparatus consists essentially of a device 52 which is a simple amplifier when the switches 53 and 54 are closed, and which forms a memory circuit when 53 and 54 are open. These electronic switches 53 and 54 are closed when the signal 18 (or its equivalent in the loop E) indicating equilibrium unbalance is sufficiently small; they open simultaneously when this signal 18 is too large, thus enabling the device 52 to retain the signal 10 in its memory and thus providing the displayed signal 55 equal to the last correct value observed for the signal 10.

The pulses which control these switches 53 and 54 are provided by a logic circuit fed by the signal 18 and the pulse 34. This logic circuit provides, at the same time, an alarm signal 56 which triggers a warning light 57 when the automatic devices for calculating R or E are in a state of equilibrium unbalance, thus informing the user that the values displayed are memorized values.

Finally, four switches 21 have been provided in order to permit the apparatus to be reset to zero.

Of course, the invention is not limited to the embodiment which has been described and represented by way of example, and the introduction of modifications therein would not go outside the scope of the invention.

I claim:

1. Automatic electronic apparatus for measuring and displaying simultaneously the resistance R to air flow through the bronchial tracts and the elastance E of the pulmonary tissue of a subject, the parameters R and E being included in the known Rohrer equation $$p(t) = R \dot{v}(t) + E v(t)$$

wherein variables $p(t)$, $\dot{v}(t)$ and $v(t)$ are instantaneous values, with reference to their mean values, of endothoracic or buccal pressure, buccal or endotracheal air flow, and volume of pulmonary air, respectively, and wherein the variables $p(t)$ and $\dot{v}(t)$ are convertible to a first voltage signal and a second voltage signal, respectively proportional to the pressure and air flow, said apparatus comprising:

a. first means for preamplifying said first voltage signal;

b. second means for preamplifying said second voltage signal;

c. first means, responsive to said preamplified first voltage signal, for correcting for slow drift of said preamplified first voltage signal to generate a third voltage signal of zero mean value of the pressure;

d. second means, responsive to said preamplified second voltage signal, for correcting for slow drift of said preamplified second voltage signal and for integrating said preamplified second voltage signal to generate a fourth voltage signal of zero mean value of the air volume;

e. first automatic computing means, responsive to said third voltage signal and said preamplified second voltage signal, for generating a fifth alpha voltage signal representing R and a sixth error signal which is cancelled when said fifth voltage signal represents the correct value of R;

f. second automatic computing means, responsive to said third voltage signal and said fourth voltage signal, for generating a seventh beta voltage signal representing E and an eighth error signal which is cancelled when said seventh voltage signal represents the correct value of E;

g. first means, responsive to said fifth and sixth signals, for displaying the correct value of R; and h. second means, responsive to said seventh and eighth signals, for displaying the correct value of E.

2. Apparatus according to claim 1 wherein said first means for correcting comprises:

a. a comparison amplifier means; and b. a control loop means, connected to said amplifier means, for generating a ninth signal representing the mean value of the pressure, said amplifier means subtracting said ninth signal from said preamplified first signal at each respiratory cycle of the subject, thereby producing said third signal referenced to the mean pressure value and whereby any slow drift of said preamplified first signal does not appreciably affect the accuracy of the computation of R and E.

3. Apparatus according to claim 1 wherein said second means for correcting and integrating comprises:
   a. an integrator; and
   b. a control loop means, connected to said integrator, for generating a ninth signal representing the mean value of the air volume and for subtracting said ninth signal from said preamplified second signal at each respiratory cycle of the subject, said integrator integrating the resultant signal of said subtraction to produce said fourth signal referenced to the mean volume value, whereby any slow drift of said preamplified second signal does not appreciably affect the accuracy of the computation of R and E.

4. Apparatus according to claim 1 wherein said first automatic computing means comprises:
   a. a first differential amplifier means;
   b. third means, responsive to said preamplified second signal and said fifth signal, for generating a ninth signal which is proportional, by said fifth signal, to said preamplified second signal, said first differential amplifier means generating a first difference signal corresponding to the difference between said ninth signal and said third signal;
   c. first means for multiplying said first difference signal and said preamplified second signal to produce a tenth signal;
   d. first means for integrating said tenth signal over the whole period of each respiratory cycle of the subject to produce said sixth error signal; and
   e. first means for memorizing said integrated tenth signal to provide said fifth signal, whereby, after a few respiratory cycles, a stable equilibrium condition is obtained when the result of integration by said first means for integrating is zero, indicating a constant value of said fifth signal and hence the correct value of R.

5. Apparatus according to claim 4 wherein said second automatic computing means comprises:
   a. a second differential amplifier means;
   b. fourth means, responsive to said fourth signal and said seventh signal, for generating an eleventh signal which is proportional, by said seventh signal, to said fourth signal, said second differential amplifier means generating a second difference signal corresponding to the difference between said eleventh signal and said third signal;
   c. second means for multiplying said second difference signal and said fourth signal to produce a twelfth signal;
   d. second means for integrating said twelfth signal over the whole period of each respiratory cycle of the subject to produce said eighth error signal; and
   e. second means for memorizing said integrated twelfth signal to provide said seventh signal, whereby, after a few respiratory cycles, a stable equilibrium condition is obtained when the result of integration by said second means for integrating is zero, indicating a constant value of said seventh signal and hence the correct value of E.

6. Apparatus according to claim 1 wherein said first means for displaying comprises:
   a. a first alarm means; and
   b. a first logic circuit means, responsive to said sixth signal, for activating said first alarm means when said sixth signal is not near 0 by a predetermined amount; and
   c. first means, responsive to said fifth signal and connected to said first logic circuit means, for showing the correct value of R when said sixth signal is near 0 by said predetermined amount, said first alarm means being deactivated when said sixth signal is near 0 by said predetermined amount.

7. Apparatus according to claim 6 wherein said second means for displaying comprises:
   a. a second alarm means;
   b. a second logic circuit means, responsive to said eighth signal, for activating said second alarm means when said eighth signal is not near 0 by a predetermined amount; and
   c. a second means, responsive to said seventh signal and connected to said second logic curcuit means, for showing the correct value of E when said eighth signal is near 0 by said predetermined amount, said second alarm means being deactivated when said eighth signal is near 0 by said predetermined amount.

8. Automatic computing apparatus for generating a signal R, which is the resistance to air flow through the bronchial tracts of a subject, in response to first signals representing endothoracic or buccal pressure and the zero mean value of the pressure, and in response to second signals representing the variation in buccal or endotracheal air flow, comprising:
   a. differential amplifier means;
   b. first means for generating alpha signals;
   c. second means, responsive to said alpha signals and said second signals, for generating third signals which are proportional, by said alpha signals, to said second signals, said differential amplifier means providing difference signals corresponding to the difference between said third signals and said first signals;
   d. means for multiplying said difference signals and said second signals to produce fourth signals; and
   e. means for integrating said fourth signals over the whole period of each respiratory cycle of a subject to produce fifth error signals which are cancelled when said alpha signals represent a correct value of signal R, said first means for generating including means for memorizing said integrated fourth signals to provide said alpha signals.

9. Automatic computing apparatus for generating a signal E, which is the elastance of the pulmonary tissue of a subject, in response to first signals representing endothoracic or buccal pressure and a zero mean value of the pressure, and in response to second signals representing the volume of pulmonary air and the zero mean value of the air volume, comprising:
   a. a differential amplifier means;
   b. first means for generating beta signals;
   c. second means, responsive to said beta signals and said second signals, for generating third signals which are proportional, by said beta signals, to said second signals, said differential amplifier means providing difference signals corresponding to the difference between said third signals and said first signals;
   d. means for multiplying said difference signals and said second signals to produce fourth signals; and e. means for integrating said fourth signals over the whole period of each respiratory cycle of a subject to produce fifth error signals which are cancelled when said beta signals represent a correct value of signal E, said first means for generating including means for memorizing said integrated fourth signals to provide said beta signals.

* * * * *